United States Patent [19]

Beuke et al.

[11] Patent Number: 5,378,668
[45] Date of Patent: Jan. 3, 1995

[54] PROCESS FOR REACTIVATING AMMOXIDATION CATALYSTS

[75] Inventors: Brigitte Beuke; Jens Herwig, both of Cologne; Ernst-Friedrich Neeb; Nikolaus Paris, both of Dormagen, all of Germany

[73] Assignee: EC Erdolchemie GmbH, Cologne, Germany

[21] Appl. No.: 46,045

[22] Filed: Apr. 12, 1993

Related U.S. Application Data

[63] Continuation-in-part of Ser. No. 13,123, Feb. 3, 1993, abandoned, which is a continuation of Ser. No. 725,172, Jul. 3, 1991, abandoned.

[30] Foreign Application Priority Data

Jul. 13, 1990 [DE]  Germany ............................ 4022416

[51] Int. Cl.$^6$ .......................... B01J 23/94; B01J 23/92; C07C 255/08; C07C 253/24
[52] U.S. Cl. ........................................ 502/20; 502/34; 502/41; 502/54; 502/212; 558/324
[58] Field of Search ..................... 502/34, 212, 20, 41, 502/54; 558/324

[56] References Cited

U.S. PATENT DOCUMENTS

| | | | |
|---|---|---|---|
| 3,642,930 | 2/1972 | Grasselli et al. | 558/324 |
| 3,882,159 | 5/1975 | Callahan et al. | 558/324 |
| 4,052,332 | 10/1977 | D'Amore et al. | 502/212 |
| 4,148,757 | 4/1979 | Brazdil | 558/324 |
| 4,404,397 | 9/1983 | Daniel | 558/324 |
| 4,609,635 | 9/1986 | Cahavesi et al. | 502/212 |
| 4,618,593 | 10/1986 | Sasaki et al. | 502/34 |
| 4,757,038 | 7/1988 | Sasaki et al. | 502/34 |

FOREIGN PATENT DOCUMENTS 0465969  1/1992  European Pat. Off. ............. 502/34

*Primary Examiner*—Paul E. Konopka
*Attorney, Agent, or Firm*—Sprung, Horn, Kramer & Woods

[57] ABSTRACT

Molybdenum/bismuth-based fluid-bed catalysts which are used for the ammoxidation of olefins can be reactivated by addition of a mixed oxide of formula $$Mo_{20}(P, Cr)_{0.3-2.0}(Bi, Ni, Fe, Co)_{1.33-4.0}O_x$$

wherein, besides Mo, one element from component group (P, Cr) and one or more metals from component group (Bi, Ni, Fe, Co) are present, and x results from the valency requirements, the mixed oxide being applied to $SiO_2$ as support.

10 Claims, No Drawings

PROCESS FOR REACTIVATING AMMOXIDATION CATALYSTS

This is a continuation-in-part of application Ser. No. 08/013,123, filed Feb. 3, 1993, now abandoned, which is a continuation of application Ser. No. 07/725,172, filed Jul. 3, 1991, now abandoned.

BACKGROUND OF THE INVENTION

1. Field of the Invention

The invention relates to a process for reactivating catalysts which are used in a fluid-bed process for the ammoxidation of olefins. The reactivation is carried out by addition of a reactivator.

Important ammoxidation processes carried out on a large scale produce acrylonitrile or methacrylonitrile from propylene or i-butene by reaction with ammonia and oxygen. The ammoxidation catalysts hitherto available and used on a large scale can retain their high initial activities and particularly their high initial selectivities only for a few weeks, and in many cases even for only a few days, and then show a marked decrease which especially concerns the desired selectivity to (meth)acrylonitrile, whereas the total conversion of the olefin to increasingly appearing undesired by-products, such as CO, $CO_2$, acetonitrile or hydrogen cyanide, remains in general unchanged.

2. Description of the Related Art

To limit the yield losses of the desired nitriles, various methods for reactivating the ammoxidation catalysts have been developed. Thus, in DE-OS (German Published Specification) 2,435,031, a reactivator is used which is formed from 85% by weight of $MoO_3$ and 15% by weight of $SiO_2$ and which can raise the yield of 63% of acrylonitrile by addition of 6.4% by weight of reactivator, relative to the deactivated catalyst, to 70% acrylonitrile yield.

High additions of molybdenum oxide are also used in the process of DE-OS (German Published Specification) 3,311,521; in the process mentioned, these amount to about 2.2% by weight, relative to the deactivated ammoxidation catalyst, and the acrylonitrile yield can rise, for example, from 65.5% to 72.5%.

A further reactivation method is described in DE-OS (German Published Specification) 2,717,579, the deactivated ammoxidation catalyst being treated with an impregnation solution which contains molybdenum and bismuth in a molar ratio of 0.5–20:1 and optionally phosphoric acid. The treated catalyst is calcined and then used again. In the optimum case, the selectivity for acrylonitrile is here raised from 76.7% to 92.8% of the propylene conversion, so that the acrylonitrile yield can rise up to 71.2%.

A further reactivation is achieved, by the process of DE-OS (German Published Specification) 3,123,521, in such a way that the recalcined fines of a spent ammoxidation catalyst are added as reactivator in a ratio of 1:3 to a deactivated catalyst. In this way, yield improvements of about 5% can be achieved.

Quite generally, the acrylonitrile yield can of course also be held at a high level or raised from decreased values to a higher level by quantitative or at least partial replacement of deactivated catalyst by fresh catalyst. The disadvantage of this last-mentioned method is represented by the relatively large quantities which are required to produce or maintain this effect. Thus, a quantity of 50% by weight of the catalyst originally charged into the reactor is necessary per year even for only partial replacement.

SUMMARY OF THE INVENTION

Surprisingly, it has now been found that both a deactivated ammoxidation catalyst and an ammoxidation catalyst reactivated in a known manner are rendered capable of further yield improvements if the mixed oxide on an $SiO_2$ support, described further below, is used as the reactivator.

A process for the reactivation of molybdenum/bismuth-based fluid-bed catalysts, which are used for the ammoxidation of olefins, by addition of a reactivator has been found, which is characterized in that the reactivator used is a mixed oxide, applied to $SiO_2$ as support, of the formula

$$Mo_{20}(P, Cr)_{0.3-2.0}(Bi, Ni, Fe, Co)_{1.33-4.0}O_x$$

wherein, besides Mo, one element from component group (P, Cr) and one or more metals from component group (Bi, Ni, Fe, Co) are present, and said reactivator has a specific surface area of 1–100 $m^2/g$.

x results from the valency of requirements.

DETAILED DESCRIPTION OF THE INVENTION

The quantity of oxygen in the mixed oxide and hence the index x results from the valency requirements. A person skilled in the art of oxidation catalysts is familiar with these requirements. In this case, it is assumed that the mentioned elements are in the highest stable valency under the oxidation conditions.

The weight ratio of the mixed oxide to the $SiO_2$ support is 0.25–1.5:1, preferably 0.5–1.2:1.

For preparing the reactivator to be used according to the invention, the $SiO_2$ support can be sprayed, impregnated or mixed with one or more aqueous solutions of the element compounds leading to the mixed oxide, in a manner known in principle. The impregnated $SiO_2$ support thus obtained is then dried and subsequently calcined.

A suitable $SiO_2$ support is fine $SiO_2$ of particle size class $<200\mu$, for example 10–200$\mu$, preferably 30–160$\mu$. It is, however, also possible to use an SiO sol as the $SiO_2$ support, and the suspension formed by addition of aqueous solutions of the element compounds is brought by spray-drying to the same particle size which is obtained by using the finely disperse $SiO_2$ of the said particle size class.

For the impregnation, aqueous solutions of the element compounds are used, for example those of ammonium heptamolybdate, ammonium dihydrogen phosphate, chromium (III) nitrate, bismuth nitrate and nitrates of the metals Ni, Fe and Co. In place of the nitrates, salts of other anions, for example the acetates, can in principle also be used, if such anions are volatile during the final calcination and if they give water-soluble salts. In the case that the aqueous solutions tend to hydrolysis and to preciptation of oxidic element compounds, the state of a true solution can be maintained by addition of a little nitric acid. The content of element compounds in the aqueous solutions can in principle vary within wide limits but, in order to avoid handling of large quantities of water, is applied in relatively high concentration ranges up to just below the saturation concentration, for example as an approximately 50% strength by weight aqueous solution.

The internal surface area of the finely dispersed $SiO_2$ is in general 100–600 $m^2/g$, preferably 250–500 $m^2/g$.

The mixed oxide contains in principle molybdenum and an element from the component group (P, Cr) and one or more metals from component group (Bi, Ni, Fe, Co). Preferably, also only one metal from the component group (Bi, Ni, Fe, Co) is present in the mixed oxide.

One or more elements from the component groups in brackets can be present simultaneously.

The order of applying the various component groups for the mixed oxide to the $SiO_2$ support can in principle be as desired. It has, however, proved to be advantageous first to impregnate with molybdenum and the component group (P, Cr), in the form of their compounds, and then to impregnate with the component group (Bi, Ni, Fe, Co) in each case in the form of suitable compounds.

The subsequent drying can take place at 90°–150° C., preferably at 110°–130° C. if appropriate under a reduced pressure.

After drying, the impregnated $SiO_2$ support is calcined at a temperature of 600°–800° C., preferably 650°–750° C., for a time in the range of 5–60 minutes, selected as a function of the calcination temperature, in such a way that the reactivator thus obtained with elimination of the above-mentioned anions (for example nitrate or acetate) has a specific surface area of 1–100 $m^2/g$, preferably 5–50 $m^2/g$, particularly preferably 10–30 $m^2/g$. The dependence of the desired specific surface area of the calcination temperature and calcination time is known in principle to those skilled in the art and can be determined reliably by simple preliminary tests.

The molybdenum/bismuth-based fluid-bed catalysts, which are to be reactivated, for the ammoxidation of olefins are those known and industrially used, which are described, for example, in U.S. Pat. Nos. 3,642,930 and 3,471,556 and in DE-OS (German Published Specification) 2,147,480. The catalysts described therein are complex oxides containing, besides Mo and Bi, various elements, such as Fe, one or more from the group (alkali metals, alkaline earth metals, rare earth metals), one or more from the group (P, As, Sb), one or more from the group (Co, Ni) and further can contain Ta and Nb. In a particularly preferred manner, the process according to the invention is applied to ammoxidation catalysts which are used for the conversion of propylene into acrylonitrile.

A great advantage of the process according to the invention is the relatively small specific reactivator quantity in the range of 0.1–5% by weight, preferably 0.4–2% by weight, per reactivation, relative to the ammoxidation catalyst to be reactivated. Equally astounding is the sustained effect of the reactivation by the process according to the invention, so that a further addition/renewed reactivation becomes necessary only after a few weeks, whereas a conventional catalyst reactivation with fresh catalyst requires periodic refreshing at intervals of a few days, in order to achieve the same effect. Thus, it is typical to carry out a renewed reactivation by the process according to the invention at intervals of a few weeks, (about 4–6 weeks), so that about 10–13, and frequently only 10 or 11, reactivations are necessary per year. Of course, it is also possible to use correspondingly smaller quantities of the reactivator to be used according to the invention at shorter intervals. In the example of acrylonitrile, the consumption amounts to about 0.05–0.2 kg of reactivator per tonne of acrylonitrile.

The achievable increase in the yield of (meth)acrylonitrile depends on the quantity of added reactivator and on the yield level to which the ammoxidation catalyst to be reactivated had fallen. In the case that the yield level had not fallen to an unduly low value, the extent of reactivation is less than in the case of a catalyst which has fallen to a lower level. Typical values of the yield increase ($\Delta$ yield) are an increase from 75 to 78% or from 72 to 75–76%. The indicated relationships between yield level, reactivator quantity and $\Delta$ yield are explained in more detail in the illustrative examples.

A further advantage of the process according to the invention is the simple composition and ease of preparation of the reactivator as compared with a fresh catalyst of more complicated structure, so that improved economics of the (meth)acrylonitrile manufacture are also assured in this respect.

Example A (Reactivator preparation, laboratory scale)

15.03 g of $SiO_2$ support material (Messrs. Hermann) of particle size class <160$\mu$ were initially introduced and impregnated with 14.96 g of ammonium heptamolybdate (4 $H_2O$) in 15 ml of water and 0.325 g of ammonium dihydrogen phosphate in 4 ml of water. 5.48 g of bismuth nitrate pentahydrate in 7 g of water were then added for further impregnation.

After the second impregnation, the mixture was dried at 130° C. and then calcined for 15 minutes at 750° C., a specific surface area of 14.7 $m^2/g$ being obtained.

The other reactivators from the table further below were prepared by the same preparation scheme.

Example B (Reactivator preparation, large industrial scale)

18.31 kg of $SiO_2$ sol (Na-stabilized, 40% strength by weight) were mixed with 3.17 kg of ammonium dihydrogen phosphate solution (5% strength by weight), 21.44 kg of ammonium heptamolybdate solution (34% strength by weight) and 7.08 kg of bismuth nitrate solution (37.7% strength by weight in 30% strength by weight nitric acid). The mixture was fed to a continuously operating spray-drier to remove the water and to obtain a particle size distribution in the desired range of 10–150$\mu$ with approximately spherical geometry of the particles.

The spray-dried material was freed of nitrate during 20 minutes in a discontinuous rotary furnace at 500° C. It was then calcined for 10 minutes at 690° C., a specific surface area of 15.7 $m^2/g$ being obtained.

Application Examples and Comparison Examples

General procedure (laboratory reactor)

In a 1600 ml steel reactor having an L/D ratio of 29, 550 g of a molybdenum/bismuth-based ammoxidation catalyst were subjected to 217 g/hour of air, 14.5 g/hour of ammonia and 30.24 g/hour of propylene at 445° C. and under 1.8 bar (absolute).

The reaction gas was analyzed and evaluated by balancing methods for conversion, selectivity, ACN yield and $\Delta$ yield (yield increase).

Application Examples and Comparison Examples

General procedure (large industrial-scale reactor)

In a large industrial-scale reactor of 22.56 m height and 4 m diameter, 28.6 tonnes of a molybdenum/bismuth-based ammoxidation catalyst were subjected to 18 tonnes/hour of air, 1.2 tonnes/hour of ammonia and 2.57 tonnes/hour of propylene. Under a reaction pressure of 1.98 bar (absolute), the temperature was maintained at 445° C. by means of cooling layers in which water vaporizes.

The reaction gas was analyzed and evaluated by balancing methods as indicated.

Table of Examples 1–9 (for comparison), 10–21 (application of the same reactivator to different catalysts) and 22–34 (application of different catalysts) and 22–34 (application of different reactivators).

Examples 1, 3 and 5–9 show the catalytic action of an Mo/Bi-based ACN catalyst exhausted to different extents; this catalyst is the type C49 of Standard Oil of Ohio Co. (Sohio), the constitution of which is not completely known but which is understood to fall under U.S. Pat. No. 3,642,930. Example 2 shows the addition of 0.7% by weight of fresh catalyst to the catalyst according to Example 1; Example 4 shows the catalytic effect of the said reactivator by itself (100%). The ratio of the components is that of the atom numbers.

$$Mo_{20}(P, Cr)_{0.3-2.0}(Bi, Ni, Fe, Co)_{1.33-4.0}O_x$$

wherein, besides Mo, one element from component group (P, Cr) and one metal from component group (Bi, Ni, Fe, Co) are present, x results from the valency requirements, said reactivator has a specific surface area of 5–50 m$^2$/g and is added in an amount of 0.4–2% by weight, relative to the amount of said ammoxidation catalyst to be reactivated, and wherein said ammoxidation catalysts are complex oxide catalysts containing Mo, Bi, Fe, and a) one or more members of the group consisting of alkali metals, alkaline earth metals and rare earth metals, and b) one or more members of the group consisting of P, As and Sb, and c) one or more members of the group consisting of Co and Ni, and optionally d) one or more members of the group consisting of Ta and Nb.

| Examples | No. | Reactivator quantity, % by weight | Component:Ratio | Conversion % | Selectivity % | ACN yield % | Δ Yield % |
|---|---|---|---|---|---|---|---|
| Comparison | 1 | — | — : — | 99.4 | 73.1 | 75.9 | — |
| Example | 2 | 0.7 | Fresh cat.:Sohio :C49 | 99.8 | 72.1 | 75.7 | — |
|  | 3 | — | — : — | 98.8 | 74.3 | 73.4 | — |
|  | 4 | 100 | Mo, Bi, P:20:2.7:0.7 | 85.5 | 68.6 | 59.9 | — |
|  | 5 | — | — : — | 99.3 | 72.0 | 73.8 | — |
|  | 6 | — | — : — | 99.3 | 70.6 | 75.3 | — |
|  | 7 | — | — : — | 99.2 | 70.9 | 74.8 | — |
|  | 8 | — | — : — | 99.5 | 69.8 | 75.8 | — |
|  | 9 | — | — : — | 99.6 | 70.2 | 73.2 | — |

| Examples | No. | Base catalyst Ex. No. | Reactivator quantity % by wt. | Component:Ratio | Conversion % | Selectivity % | ACN yield % | Δ yield % |
|---|---|---|---|---|---|---|---|---|
| Appl. Ex. | 10 | 1 | 0.7 | Mo, Bi, P:20:2.7:0.7 | 98.7 | 74.8 | 77.8 | 1.9 |
|  | 11 | 3 | 0.7 | Mo, Bi, P:20:2.7:0.7 | 98.9 | 75.8 | 75.0 | 1.6 |
|  | 11a | 3 | 0.7 | Mo, Bi, P:20:2.7:0.7 | 98.5 | 75.6 | 74.5 | 1.1 |
|  | 12 | 5 | 1.4 | Mo, Bi, P:20:2.7:0.7 | 99.0 | 73.8 | 78.1 | 4.3 |
|  | 13 | 6 | 0.5 | Mo, Bi, P:20:2.7:0.7 | 99.3 | 73.2 | 76.8 | 1.5 |
|  | 14 | 6 | 1.0 | Mo, Bi, P:20:2.7:0.7 | 99.0 | 72.7 | 77.1 | 1.8 |
|  | 15 | 6 | 1.5 | Mo, Bi, P:20:2.7:0.7 | 98.5 | 72.8 | 76.7 | 1.4 |
|  | 16 | 7 | 0.6 | Mo, Bi, P:20:2.7:0.7 | 98.7 | 74.8 | 76.1 | 1.3 |
|  | 17 | 8 | 1.0 | Mo, Bi, P:20:2.7:0.7 | 99.4 | 73.3 | 77.4 | 1.6 |
|  | 18 | 8 | 1.5 | Mo, Bi, P:20:2.7:0.7 | 99.0 | 75.8 | 78.2 | 2.4 |
|  | 19 | 9 | 0.4 | Mo, Bi, P:20:2.7:0.7 | 99.5 | 72.3 | 75.5 | 2.3 |
|  | 20 | 9 | 0.6 | Mo, Bi, P:20:2.7:0.7 | 99.5 | 72.7 | 76.2 | 3.0 |
|  | 21 | 9 | 0.8 | Mo, Bi, P:20:2.7:0.7 | 99.5 | 73.1 | 76.2 | 3.0 |
|  | 22 | 5 | 1.3 | Mo, Ni, P:20:4:0.7 | 99.1 | 72.6 | 77.8 | 4.0 |
|  | 23 | 5 | 1.2 | Mo, Co, P:20:2.7:0.7 | 99.0 | 72.3 | 77.2 | 3.4 |
|  | 24 | 5 | 1.2 | Mo, Fe, P:20:2.7:0.7 | 98.8 | 73.7 | 77.2 | 3.4 |
|  | 25 | 5 | 1.1 | Mo, Bi, P:20:1.33:0.44 | 98.8 | 71.2 | 76.5 | 2.7 |
|  | 26 | 5 | 1.0 | Mo, Bi, P:20:3.3:1.66 | 99.1 | 73.5 | 77.8 | 4.0 |
|  | 27 | 5 | 1.25 | Mo, Co, P:20:3.3:1.66 | 98.8 | 73.9 | 77.7 | 3.9 |
|  | 28 | 5 | 1.5 | Mo, Bi, P:20:4:0.7 | 98.6 | 73.5 | 77.2 | 3.4 |
|  | 29 | 5 | 1.2 | Mo, Co, P:20:4:0.7 | 99.4 | 72.5 | 77.3 | 3.5 |
|  | 30 | 5 | 1.0 | Mo, Fe, P:20:4:0.7 | 99.2 | 71.8 | 77.4 | 3.6 |
|  | 31 | 7 | 1.0 | Mo, Bi, Cr:20:2.7:0.7 | 99.2 | 74.4 | 77.7 | 3.1 |
|  | 32 | 7 | 1.0 | Mo, Ni, P:20:4:0.7 | 99.3 | 73.8 | 77.4 | 2.6 |
|  | 33 | 7 | 1.0 | Mo, Fe, P:20:4:0.7 | 99.2 | 73.6 | 77.7 | 3.1 |
|  | 34 | 7 | 2.0 | Mo, Co, P:20:4:0.7 | 99.1 | 74.2 | 76.5 | 1.7 |

All reactivators of Examples 22–34 have a specific surface area of 10–30 m$^2$/g

What is claimed is:

1. A process for reactivating molybdenum/bismuth-based fluid-bed ammoxidation catalysts, which are used for the ammoxidation of olefins, by addition of a reactivator, wherein the reactivator used is a mixed oxide, applied to SiO$_2$ as support, of the formula 2. The process of claim 1, wherein the weight ratio of the mixed oxide to the SiO$_2$ support is 0.25–1.5:1.

3. The process of claim 2, wherein the weight ratio of the mixed oxide to the SiO$_2$ support is 0.5–1.2:1.

4. The process of claim 1, wherein the SiO$_2$ support is sprayed, impregnated or mixed with one or more aqueous solutions of the element compounds leading to the mixed oxide, then dried and finally calcined at temperatures in the range of 600°–800°.

5. The process of claim 4, wherein the $SiO_2$ support used is of a particle size class <200μ.

6. The process of claim 5, wherein the $SiO_2$ support used is of a particle size class of 10–200μ.

7. The process of claim 6, wherein the $SiO_2$ support used is of a particle size class of 30–160μ.

8. The process of claim 4, wherein $SiO_2$ sol is used as the $SiO_2$ support, and the reactivator, after application of the element compounds leading to the mixed oxide, is finished by subsequent spray-drying.

9. The process of claim 1, wherein the reactivator is calcined in such a way that it is given a specific surface area of 10–30 $m^2/g$.

10. The process of claim 1, wherein the ammoxidation of olefins is that of propylene.

* * * * *